US010046090B2

(12) United States Patent
Burden, Jr.

(10) Patent No.: US 10,046,090 B2
(45) Date of Patent: Aug. 14, 2018

(54) PROCESSED BONE PARTICLE COMPOSITIONS AND RELATED METHODS

(71) Applicant: Vivorte, Inc., Louisville, KY (US)

(72) Inventor: Robert L. Burden, Jr., Louisville, KY (US)

(73) Assignee: VIVORTE, INC., Louisville, KY (US)

( * ) Notice: Subject to any disclaimer, the term of this patent is extended or adjusted under 35 U.S.C. 154(b) by 0 days.

(21) Appl. No.: 15/028,226

(22) PCT Filed: Oct. 8, 2014

(86) PCT No.: PCT/US2014/059728
§ 371 (c)(1),
(2) Date: Apr. 8, 2016

(87) PCT Pub. No.: WO2015/054407
PCT Pub. Date: Apr. 16, 2015

(65) Prior Publication Data
US 2016/0296668 A1    Oct. 13, 2016

Related U.S. Application Data

(60) Provisional application No. 61/888,393, filed on Oct. 8, 2013.

(51) Int. Cl.
*A61K 9/16* (2006.01)
*A61L 27/36* (2006.01)
(Continued)

(52) U.S. Cl.
CPC ............ *A61L 27/3608* (2013.01); *A61F 2/28* (2013.01); *A61F 2/4644* (2013.01);
(Continued)

(58) Field of Classification Search
CPC .................................................... A61K 9/1658
See application file for complete search history.

(56) References Cited

U.S. PATENT DOCUMENTS

| 3,686,377 A | 8/1972 | Hays |
| 4,880,610 A | 11/1989 | Constantz |

(Continued)

FOREIGN PATENT DOCUMENTS

| WO | 199941440 A1 | 8/1999 |
| WO | 200166044 A2 | 9/2001 |

(Continued)

OTHER PUBLICATIONS

European Patent Office, Supplementary European Search Report and Opinion from corresponding European Application No. 11820752.1, dated Feb. 13, 2014.

(Continued)

*Primary Examiner* — Carlos A Azpuru
(74) *Attorney, Agent, or Firm* — Stites & Harbison, PLLC; Terry L. Wright

(57) ABSTRACT

Bone particle compositions and kits are provided that include a biologically-resorbable cement and a plurality of processed bone particles. A first portion of the processed bone particles in the compositions have a shape configured to interconnect with one another, while a second portion of the processed bone particles having an irregular shape. Methods for treating a bone defect are also provided wherein an effective amount of the bone particle compositions are administered to a site of a bone defect in a subject.

35 Claims, 7 Drawing Sheets

(51) Int. Cl.

| | | |
|---|---|---|
| *A61F 2/28* | (2006.01) | |
| *C09D 1/00* | (2006.01) | |
| *A61L 27/58* | (2006.01) | |
| *A61F 2/46* | (2006.01) | |
| *A61L 27/02* | (2006.01) | |
| *A61L 27/12* | (2006.01) | |
| *A61L 27/38* | (2006.01) | |
| *A61L 27/54* | (2006.01) | |
| *A61L 27/42* | (2006.01) | |
| *A61F 2/30* | (2006.01) | |

(52) U.S. Cl.
CPC .......... *A61K 9/1658* (2013.01); *A61L 27/025* (2013.01); *A61L 27/12* (2013.01); *A61L 27/365* (2013.01); *A61L 27/3683* (2013.01); *A61L 27/3691* (2013.01); *A61L 27/3834* (2013.01); *A61L 27/3847* (2013.01); *A61L 27/425* (2013.01); *A61L 27/427* (2013.01); *A61L 27/54* (2013.01); *A61L 27/58* (2013.01); *C09D 1/00* (2013.01); *A61F 2002/2835* (2013.01); *A61F 2002/3013* (2013.01); *A61F 2002/30166* (2013.01); *A61F 2002/30303* (2013.01); *A61F 2310/00359* (2013.01); *A61L 2300/406* (2013.01); *A61L 2300/412* (2013.01); *A61L 2300/604* (2013.01); *A61L 2300/64* (2013.01); *A61L 2430/02* (2013.01)

(56) References Cited

U.S. PATENT DOCUMENTS

| | | |
|---|---|---|
| 5,047,031 A | 9/1991 | Constantz |
| 5,129,905 A | 7/1992 | Constantz |
| 5,336,264 A | 8/1994 | Constantz |
| 5,507,813 A | 4/1996 | Dowd et al. |
| 5,559,022 A | 9/1996 | Naughton et al. |
| 5,672,346 A | 9/1997 | Srour et al. |
| 5,827,735 A | 10/1998 | Young et al. |
| 5,952,010 A | 9/1999 | Constantz |
| 5,962,028 A | 10/1999 | Constantz |
| 6,136,029 A | 10/2000 | Johnson et al. |
| 6,201,039 B1 | 3/2001 | Brown et al. |
| 6,432,436 B1 | 8/2002 | Gertzman et al. |
| 6,548,080 B1 | 4/2003 | Gertzman et al. |
| 6,599,516 B1 | 7/2003 | Knaack |
| 6,911,212 B2 | 6/2005 | Gertzman et al. |
| 7,163,691 B2 | 1/2007 | Knaack et al. |
| RE39,857 E | 9/2007 | Shimomura et al. |
| 7,270,813 B2 | 9/2007 | Shimp et al. |
| 7,291,345 B2 | 11/2007 | Winterbottom et al. |
| 7,494,950 B2 | 2/2009 | Armitage et al. |
| 7,628,851 B2 | 12/2009 | Armitage et al. |
| 2003/0009235 A1 | 1/2003 | Manrique et al. |
| 2003/0167093 A1 | 9/2003 | Xu et al. |
| 2003/0185903 A1 | 10/2003 | Cole et al. |
| 2003/0206937 A1 | 11/2003 | Gertzman et al. |
| 2004/0146543 A1 | 7/2004 | Shimp et al. |
| 2005/0084542 A1 | 4/2005 | Rosenberg et al. |
| 2005/0249773 A1 | 11/2005 | Maspero et al. |
| 2006/0030948 A1 | 2/2006 | Manrique et al. |
| 2007/0191963 A1 | 8/2007 | Winterbottom et al. |
| 2008/0033572 A1 | 2/2008 | D'Antonio et al. |
| 2008/0145392 A1 | 6/2008 | Knaack et al. |
| 2008/0188946 A1 | 8/2008 | Rosenberg et al. |
| 2010/0166879 A1 | 7/2010 | Shim et al. |
| 2010/0173846 A1 | 7/2010 | Zimmermann |
| 2010/0197636 A1 | 8/2010 | Bouler et al. |
| 2012/0053692 A1* | 3/2012 | Voor ............... A61K 35/32 623/16.11 |
| 2015/0283292 A1 | 10/2015 | Voor et al. |

FOREIGN PATENT DOCUMENTS

| | | |
|---|---|---|
| WO | 2002083194 A1 | 10/2002 |
| WO | 2004110308 A2 | 12/2004 |
| WO | WO 2004/110308 A2 * | 12/2004 |

OTHER PUBLICATIONS

Spiers, et al. "Calcium phosphate cement composites in revision hip arthroplasty," Biomaterials, 2002, vol. 26, pp. 7310-7318.

ISA/KR, International Search Report and Written Opinion issued in corresponding International Application No. PCT/US2011/049425, dated Mar. 26, 2012.

Bohner et al., "Injectability of Calcium Phosphate Pastes," Biomaterials, 2005, vol. 26, pp. 1553-1561.

Brown et al., "A new Calcium Phosphate Water Setting Cement," pp. 352-357 in Cements research progress, 1986, American Ceramic Society, Westerville, OH, 1986.

Burguera et al., "Injectable and Rapid-setting Calcium Phosphate Bone Cement with Dicalcium Phosphate Dihydrate," J Biomed Mater Res, 2006, vol. 77B, pp. 126-134.

Burguera et al., "High Early Strength Calcium Phosphate Bone Cement: Effects of Dicalcium Phosphate Dihydrate and Absorbable Fibers," J Biomed Mater Res A, Dec. 5, 2005, vol. 75(4), pp. 966-975.

Chow LC, "Calcium Phosphate Cements: Chemistry, Properties, and Applications," Mater Res Symp Proc, 2000, vol. 599, pp. 27-37.

Fernandez et al., "Modulation Porosity in Apatitic Cements by the of use of α-Tricalcium Phosphate—Calcium Sulphate Dehydrate Mixtures," Biomaterials, 2005, vol. 26, pp. 3395-3404.

Genin D. "Percolation: Theory and Applications." NIST, 2007.

Tamai et al., "Novel Hydroxyapatite Ceramics with an Interconnective Porous Structure Exhibit Superior Osteoconduction in vivo," J Biomed Mater Res, 2002, vol. 59A, pp. 110-117.

Verron et al., "Calcium Phosphate Biomaterials as Bone Drug Delivery Systems: A Review," Drug Discovery Today, 2010, vol. 15(13-14), pp. 547-552.

Xu et al., "Strong, macroporous, and in situ-setting calcium phosphate cement-layered structures," Biomaterials, 2007, vol. 28(26), pp. 3786-3796.

Xu et al., "Injectable and Macroporous Calcium Phosphate Cement Scaffold," Biomaterials, 2006, vol. 27, pp. 4279-4287.

Xu et al., "Fast Setting Calcium Phosphate—chitosan Scaffold: Mechanical Properties Biocompatibility," Biomaterials, 2005, vol. 26, pp. 1337-1348.

Xu et al., "Self-hardening Calcium Phosphate Composite Scaffold for bone Tissue Engineering," J Orthop Res, 2004, vol. 22, pp. 535-543.

Xu et al., "Fast-setting calcium phosphate scaffolds with tailored macropore formation rates for bone regeneration," J Biomed Mater Res A, 2004, vol. 68A:4, pp. 725-734.

Yokoyama et al., "Development of calcium phosphate cement using chitosan and citric acid for bone substitute materials," Biomaterials, 2002, vol. 23, pp. 1091-1101.

Zhang et al., "In-situ hardening hydroxyapatite-based scaffold for bone repair," J Mater Sci: Mater Med, 2006, vol. 7, pp. 437-445.

Zhang et al., "Effects of synergistic reinforcement and absorbable fiber strength on hydroxyapatite bone cement," J Biomed Mater Res, 2005, vol. 75A, pp. 832-840.

Xu et al., "Whisker-reinforced bioactive composites containing calcium phosphate cement fillers: effects of filler ratio and surface treatments on mechanical properties," J Biomed Mater Res, 2001, vol. 57(2), pp. 165-174.

Xu et al., "Strong and macroporous calcium phosphate cement: Effects of porosity and fiber reinforcement on mechanical properties," J Biomed Mater Res, 2001, vol. 57(3), pp. 457-466.

IP Australia, Patent Examination Report No. 1, issued in corresponding Application No. 2011293202, dated Jan. 18, 2016.

European Patent Office, Examination Report from corresponding European Application No. 11820752.1, dated Jan. 5, 2016.

ISA/US, International Search Report issued in corresponding Application No. PCT/US14/59728, dated Dec. 18, 2014.

(56) References Cited

OTHER PUBLICATIONS

European Patent Office, Extended European Search Report issued in corresponding Application No. EP14851617, dated Apr. 21, 2017.
IP Australia, Full Examination Report No. 1 issued in corresponding Application No. 2014331971, dated Jul. 14, 2017.
IP Australia, Full Examination Report No. 2 issued in corresponding Application No. 2014331971, dated Apr. 26, 2018.

* cited by examiner

PROCESSED BONE PARTICLE COMPOSITIONS AND RELATED METHODS

RELATED APPLICATIONS

This application claims priority from U.S. Provisional Application Ser. No. 61/888,393, filed Oct. 8, 2013, the entire disclosure of which is incorporated herein by this reference.

TECHNICAL FIELD

The presently-disclosed subject matter relates to processed bone particle compositions and methods for making and using the same. In particular, the presently-disclosed subject matter relates to processed bone particle compositions and related methods that make use of both a plurality of bone particles having a shape configured to interconnect with one another and a plurality of irregularly-shaped bone particles.

BACKGROUND

Over 500,000 bone graft procedures are performed annually in the United States, and approximately 2.2 million are performed worldwide with an annual cost of nearly $2.5 billion. These bone graft procedures are routinely performed to not only treat bone fractures and other bone defects, but are also routinely performed to strengthen existing bone that may be deteriorating. Typically, the bone material used for these bone graft procedures is either autograft, which is derived from the patient's own body, or allograft, which is derived from a genetically dissimilar member of the same species. In some cases though, the graft material can even be xenograft, which is taken from another species.

From a biological standpoint, autograft is the preferred type of graft material and the type of material that is most commonly used in many of the orthopedic, maxillofacial, podiatric, and dental surgeries that require bone graft procedures to be performed. Autograft bone materials also exhibit many of the preferred properties for treating a bone defect, including the ability to produce new bone from transplanted living cells and the ability to integrate with the bone tissue at the graft site. Despite these advantages, however, an autograft procedure usually requires that additional surgery be performed on a subject to acquire the graft material, which can lead to complications, such as inflammation or infection. In addition, during these surgeries, only a very limited amount of bone can be collected. As such, allograft and xenograft materials have been developed that provide benefits in terms of the quantity of materials that can be obtained, but those materials still frequently have their own complications, such as disease transmission and graft failure, thus leaving researchers looking for better alternatives.

To that end, many additional types of bone graft compositions have been recently developed, including allograft-based, ceramic-based, and polymer-based compositions. Despite the many alternative bone graft compositions available today, however, the currently-available alternative bone graft compositions generally do not possess sufficient strength while at the same time providing rapid or complete incorporation, remodeling, or resorption in the body of a subject. Furthermore, currently-available bone graft compositions do not sufficiently address how certain concentrations or shapes of bone particles can be incorporated into a bone graft composition in a manner that changes the properties of the composition itself and increases the strength, resorption rate, and rate of incorporation and remodeling of the implanted materials.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes processed bone particle compositions and methods for making and using the same. In particular, the presently-disclosed subject matter includes processed bone particle compositions and related methods that make use of both a plurality of bone particles having a shape configured to interconnect with one another and a plurality of irregularly-shaped bone particles.

In some embodiments of the presently-disclosed subject matter, a bone particle composition is provided that comprises a biologically-resorbable cement and a plurality of processed bone particles. In these compositions, a first portion of the processed bone particles is comprised of bone particles having an interconnecting shape (e.g., a dumbbell shape), while a second portion of the processed bone particles have an irregular shape. In some embodiments, the interconnecting of the first portion of shaped bone particles increases the mechanical properties of the biologically-resorbable cement. In some embodiments, the first portion of bone particles are also configured to interlock with adjacent bone particles and/or are configured to interdigitate with the biologically-resorbable cement. In some embodiments, by including both the bone particles having an interconnecting shape and the irregularly-shaped bone particles in a composition, the remodeling capabilities of the composition is increased without decreasing any of the strength and bioconnectivity potential of the compositions. In particular, in some embodiments, the composition strength and bioconnectivity can be maintained by including the first portion of bone particles having an interconnected shape, while the remodeling capabilities of the composition can be increased (without decreasing the strength) through the addition of the irregularly-shaped particles. In some embodiments, each bone particle of the second portion of bone particles has a dimension of about 1 mm. In some embodiments, each bone particle of the second portion of bone particles has a dimension of about 0.1 mm to about 1.5 mm.

With respect to the first portion of interconnecting bone particles included in the presently-disclosed compositions, in some embodiments, each bone particle of the first portion of bone particles is dumbbell-shaped, having a center portion and two enlarged end portions. For example, in some embodiments that make use of dumbbell-shaped bone particles, each dumbbell-shaped bone particle has a length of about 2.5 mm and a thickness of about 1 mm, where the width of the center portion is about 0.5 mm and where each of the two enlarged end portions has a width of about 1.5 mm. In some embodiments, each end portion of each bone particle is substantially rectangular and extends laterally away from a longitudinal axis of the center portion of the bone particle.

In other embodiments, the bone graft compositions include interconnecting bone particles where each bone particle of the first portion of bone particles includes a plurality of enlarged portions and a plurality of center portions aligned along a common longitudinal axis, with each of the enlarged portions extending laterally away from a common longitudinal axis of each center portion, and with each of the center portions interposed between respective enlarged portions. In some embodiments, a cross-section of each bone particle of the first portion of bone particles is substantially round, elliptical, square, rectangular, or triangular in shape.

With respect to the biologically-resorbable cements utilized in accordance with the presently-disclosed bone graft compositions, in some embodiments, the biologically-resorbable cement is a calcium-based cement. In some embodiments, the calcium-based cement is a calcium phosphate cement. In some embodiments, the calcium-based cement is a calcium sulfate cement.

The processed bone particles of the bone graft compositions are typically combined with the cement at a concentration of about 5 percent to about 60 percent by volume of the bone particle composition or, in some embodiments, about 5 percent to about 25 percent (e.g., about 18%) by volume of the bone particle composition. In some embodiments, the first portion of the bone particles comprises about 10% by volume of the bone particle composition, and the second portion of the bone particles comprises about 8% by volume of the bone particle composition. In some embodiments, each bone particle of the first portion of bone particles and each bone particle of the second portion of bone particles is about 5% to about 100% demineralized. In such embodiments, the processed bone particles are typically comprised of cortical bone particles. In other embodiments, however, the bone particles are comprised of cancellous bone or both cortical and cancellous bone.

Further, the processed bone particles of the presently-disclosed bone graft compositions can, in some embodiments, be selected from autograft bone particles, allograft bone particles, xenograft bone particles, and combinations thereof. In some embodiments, the compositions further comprise an osteoinductive material, an osteogenic material, or both. In some embodiments, the compositions further comprise an antibiotic. In some embodiments, the compositions further comprise a stem cell.

Further provided in some embodiments of the presently-disclosed subject matter are methods for making a bone particle composition. In some embodiments, a method for making a bone particle composition is provided that comprises the steps of: providing an intact bone (e.g., a bone diaphysis); cutting the intact bone along a length of the bone to yield a substantially flat segment of the intact bone; and cutting a first portion of bone particles from the substantially flat segment of the intact bone, where each bone particle of the first portion of bone particles has a shape configured to interconnect with one another. In some embodiments, the intact bone that is utilized can be placed in a fixture configured to secure the longitudinal axis of the intact bone parallel to the cutting plane. In this regard, in some embodiments, cutting the intact bone can include cutting the intact bone using a saw blade rotating on an axis perpendicular to the longitudinal axis of the intact bone. In some embodiments, the methods can then further comprise the step of grinding a remainder of the flat segment of bone to yield a second portion of bone particles having an irregular shape. In some embodiments, the first portion and the second portion of the bone particles can then be demineralized.

Still further provided, in some embodiments of the presently-disclosed subject matter, are methods for treating a bone defect. In some embodiments, a method for treating a bone defect is provided that includes administering an effective amount of a bone particle composition of the presently-disclosed subject matter to a site of a bone defect in a subject. In some embodiments, the bone defect is a bone void, a bone fracture, or a site of an intended bone fusion. In some embodiments, administering the bone composition to the site of the bone defect comprises filling the bone defect with the bone composition.

In yet further embodiments of the presently-disclosed subject matter, kits are provided. In some embodiments, kits are provided that comprise a biologically-resorbable cement powder and a plurality of processed bone particles, where a first portion of the processed bone particles have a shape configured to interconnect with one another, and where a second portion of the processed bone particles have an irregular shape. In some embodiments, the processed bone particles are lyophilized. In this regard, in some embodiments, the kits further include water or another an aqueous vehicle for adding to the biologically-resorbable cement powder, the processed bone particles, or both the biologically-resorbable cement powder and the processed bone particles. In some embodiments, the kit further comprises instructions for mixing the processed bone particles and the biologically-resorbable cement powder.

Further features and advantages of the present invention will become evident to those of ordinary skill in the art after a study of the description, figures, and non-limiting examples in this document.

DESCRIPTION OF EXEMPLARY EMBODIMENTS

Figure 1A:
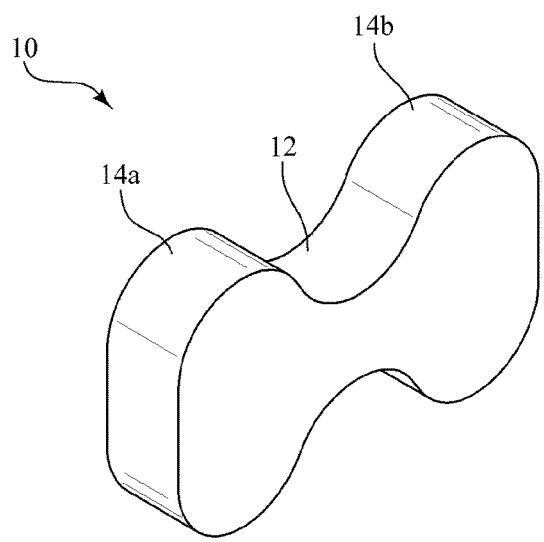
FIG. 1A is a perspective view of a dumbbell-shaped bone particle made in accordance with the presently-disclosed subject matter.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter. Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

In some embodiments of the presently-disclosed subject matter, a bone particle composition is provided that includes materials added to a biologically-resorbable cement, which allow the cement structure that forms, after it sets in the body, to more rapidly incorporate and remodel. In some embodiments, the materials that are added to the compositions include processed bone particles, which allow the compositions to remodel faster when placed in a subject, but also allow for infiltration of the cement structure by cells, blood, and other such bodily fluids and structures.

Figure 2:
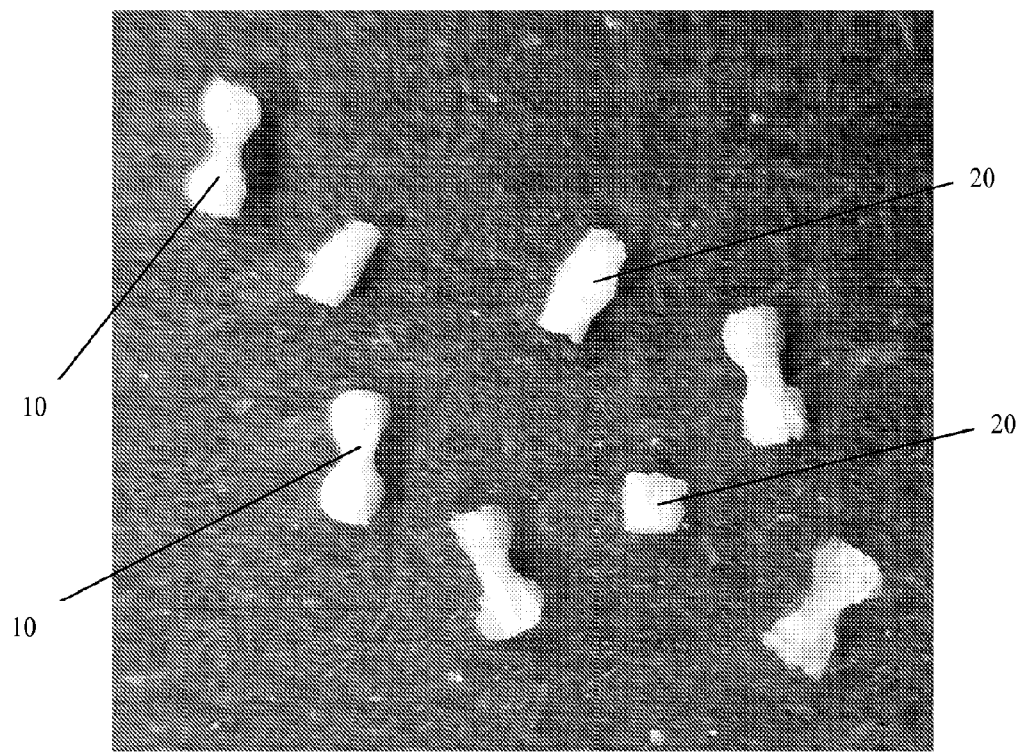
FIG. 2 is an image of processed bone particles made in accordance with the presently-disclosed subject matter, and including a plurality of the dumbbell-shaped bone particles shown in FIG. 1A and a plurality of irregularly-shaped bone particles.

In some embodiments of the presently-disclosed subject matter, bone particle compositions are provided that comprise a biologically-resorbable cement and a plurality of processed bone particles. As described in further detail below, in some embodiments of these compositions, and as shown in the exemplary composition in FIG. 2, a first portion of the processed bone particles includes processed bone particles 10 having a shape configured to interconnect and interlock with other bone particles having an interconnecting shape, while a second portion of the processed bone particles includes bone particles 20 having an irregular shape.

The term "biologically-resorbable cement" is used herein to refer to any biological cement, such as a bone substitute cement, that is capable of being broken down and assimilated by the body of a subject, and that is substantially non-toxic in the in vivo environment of its intended use such that it is not substantially rejected by the subject's physiological system (i.e., is non-antigenic or biocompatible). This can be gauged by the composition's toxicity, infectivity, pyrogenicity, irritation potential, reactivity, hemolytic activity, carcinogenicity and/or immunogenicity. A biologically-resorbable cement, when introduced into a bone of a majority of subjects, will not cause an undesirably adverse, long-lived or escalating biological reaction or response, and is distinguished from a mild, transient inflammation which typically accompanies surgery or implantation of foreign objects into a living organism.

As would be recognized by those skilled in the art, a "cement" is a product that is produced as a result of the setting of a paste that is formed by mixing a powdered component with water or another aqueous vehicle. A number of biologically-resorbable cements can be formed by mixing a powder component with water or another aqueous vehicle and then used in accordance with the presently-disclosed bone particle compositions, including, but not limited to, ceramics-based cements, calcium-based cements, magnesium ammonium-based cements, and the like. In some embodiments of the presently-disclosed compositions, the biologically-resorbable cement is a calcium-based cement, such as a calcium sulfate cement or a calcium phosphate cement, where the powdered component is comprised of a calcium-based compound. In some embodiments, the calcium-based cement is a calcium phosphate cement. In other embodiments, the calcium-based cement is a calcium sulfate cement.

The phrase "calcium phosphate cement" is used herein to refer to a cement where the powdered component of the cement is comprised of a calcium phosphate compound or a mixture of calcium and/or phosphate compounds. Exemplary calcium phosphate compounds or mixtures of calcium compounds and/or phosphate compounds that can be mixed with water or another aqueous vehicle and used in accordance with the presently-disclosed subject matter include, but are not limited to: tricalcium phosphate ($Ca_3(PO_4)_2$; TCP), including alpha-TCP, beta-TCP, and biphasic calcium phosphate containing alpha- and beta-TCP; amorphous calcium phosphate (ACP); monocalcium phosphate ($Ca(H_2PO_4)_2$; MCP) and monocalcium phosphate monohydrate ($Ca(H_2PO_4)_2.H_2O$; MCPM); dicalcium phosphate ($CaHPO_4$; DCP), dicalcium phosphate anhydrous ($CaHPO_4$; DCPA) and dicalcium phosphate dihydrate ($CaH_5PO_6.2H_2O$; DCPD); tetracalcium phosphate (($Ca_4PO_4)_2O$; TTCP); octacalcium phosphate ($Ca_8(PO_4)_4HPO_4)_2.5H_2O$; OCP); calcium hydroxyapatite ($Ca_{10}(PO_4)_6(OH)_2$; CHA); calcium oxyapatite ($Ca_{10}(PO_4)_6O$; COXA); calcium carbonate apatite ($Ca_{10}(PO_4)_6CO_3$; CCA); and calcium carbonate hydroxyapatites (e.g., $Ca_{10}(PO_4)_5(OH)(CO_3)_2$ and $Ca_{10}(PO_4)_4(OH)_2(CO_3)_3$; CCHA). Additional calcium phosphates useful herein also include calcium-deficient calcium phosphates in which the molar or mass ratio of Ca:P is reduced by about 20% or less, about 15% or less, or about 10% or less, relative to the corresponding calcium non-deficient species, examples of which include calcium-deficient hydroxyapatites, e.g., $Ca_{10-x}(HPO_4)_x(PO_4)_{6-x}(OH)_{2-x}$ ($0 \leq X \leq 1$) (CDHA); calcium-deficient carbonate hydroxyapatites (CDCHA); calcium-deficient carbonate apatites (CDCA); and other calcium phosphate compounds and salts known to be useful in the field of bone graft materials, e.g., calcium polyphosphates; and calcium-, phosphate-, and/or hydroxyl "replaced" calcium phosphates. In some embodiments, the calcium-phosphate cement is a hydroxyapatite cement. For further explanation and guidance regarding calcium phosphate cements, see, e.g., Ambard, et al. Journal of Prosthodontics. 15(5): 321-326 (2006).

The phrase "calcium sulfate cement" is used herein to refer to a cement where the powdered component of the cement is comprised of a calcium sulfate compound or a mixture of calcium and/or sulfate compounds. Exemplary calcium sulfate compounds or mixtures of calcium compounds and/or sulfate compounds that can be mixed with water or another aqueous vehicle and used in accordance with the presently-disclosed subject matter include, but are not limited to: calcium sulfate ($CaSO_4$); calcium sulfate dihydrate ($2CaSa_4.2H_2O$); and calcium sulfate hemihydrate ($CaSO_4.\frac{1}{2}H_2O$). For further explanation and guidance regarding calcium sulfate cements, see, e.g., Bohner, European Cells & Materials, Vol. 20, 2010, pages 1-12.

Turning now to the processed bone particles that are included in the presently-disclosed bone graft compositions, the phrase "processed bone particles" is used herein to refer to pieces of bone that are derived from an intact bone, or part of an intact bone, and have been modified to produce pieces of bone with a desired level of mineralization, a desired size, and/or a desired shape, such that the pieces of bone can be combined with a suitable cement and applied to the site of a bone defect, as described in detail below. In some embodiments, the processed bone particles are of a size and shape that allows a prescribed mixture of cement (e.g., calcium phosphate cement) and processed bone particles to flow in a paste-like consistency, similar to the handling characteristics of processed cement. In some embodiments, the processed bone particles are from an autograft bone source, an allograft bone source, a xenograft bone source, or combinations thereof.

To produce an exemplary bone particle composition of the presently-disclosed subject matter, an intact bone is first obtained and is refined into a number of discrete particles. The term "intact bone" is used herein to refer to whole bones or segments of whole bones whose structures have not been substantially altered, broken, or impaired prior to being used to produce a bone particle in accordance with the presently-disclosed subject matter. In some embodiments, the intact bone used to produce the bone particles is selected from a tibia, fibula, femur, humerous, radius, ulna, or rib bone. For example, in some embodiments of the presently-disclosed subject matter, a piece of an intact long bone (e.g., a tibia or femur) is first obtained, and is placed in a computer numerically-controlled (CNC) milling machine. The bone is secured in the CNC machine using a fixture designed to rigidly hold the diaphysis of the intact bone parallel to a bench top on which the refining of the intact bone is to occur. The fixture is also designed to have a minimum interface with the bone segment so as not to interfere with the subsequent cutting and refining of the bone.

After placing the intact bone in the fixture, a thin disc saw blade capable of cutting the intact bone without splintering or otherwise splitting the bone (e.g., a diamond-sintered, diamond-embedded, or a fine tooth saw blade) is used to cut the intact bone into flat segments (e.g., 1 mm thick). In some embodiments, the thin disc saw blade cuts the intact bone by rotating on an axis perpendicular to the axis of the bone. Once the flat segments of bone have been produced, the flat segments are then exposed to a mechanical punch whereby a tool and die punching method is used to cut the flat bone segments into a desired interconnecting shape having a thickness of the produced flat segment of bone (e.g., a dumbbell-shaped bone particle having a length of about 2.5 mm, a thickness of about 1 mm, a central portion with a width of about 0.5 mm, and two enlarged end portions with a width of about 1.5 mm, see, e.g., FIG. 1A). The remainder of the flat segments of bone are then ground in a grinder to produce a plurality of irregular bone particles. In certain embodiments, the bone particles can be cycled through the grinder and sieved a number of times so as to produce irregularly-shaped bone particles having a desired dimension. Of course, other techniques, including lathe, laser cutting, and other techniques can also be used to produce bone particles having a desired interconnecting shape and can be used without departing from the spirit and scope of the subject matter described herein.

The phrase "irregularly-shaped" when used herein in reference to bone particles refers to bone particles having an asymmetric shape and whose dimensions are not uniform or symmetrical across the bone particles. In some embodiments, each of the irregularly-shaped bone particles has a maximum dimension across a portion of the irregularly-shaped bone particle of about 0.1 mm to about 1.5 mm. In some embodiments, each of the irregularly-shaped bone particles that are produced have a dimension of about 1 mm.

Regardless of the dimensions of the irregularly-shaped bone particles, after both portions of bone particles have been formed, the cement mixtures of the bone particle compositions are generally formed by mixing the powdered component of the cement with water or another aqueous vehicle. In this regard, once the processed bone particles (i.e., the specially-shaped and irregularly-shaped bone particles) are formed, the bone particles are then mixed with the cement at a desired concentration, as described further below. The term "aqueous vehicle" is used herein to refer to any fluid, such as water, that can be mixed with a powdered component of a cement to form a suitable paste of a biologically-resorbable cement. Of course, the aqueous vehicle must also be substantially non-toxic in the in vivo environment of its intended use such that it is not substantially rejected by the subject's physiological system. In addition to water, such aqueous vehicles can include, but are not limited to, buffered saline solutions, sodium phosphate monobasic monohydrate ($NaH_2PO_4.H_2O$) solutions, sodium phosphate dibasic ($Na_2HPO_4$) solutions, glycerol solutions, and the like.

Typically, the amount of water or other aqueous vehicle that is mixed with the powdered component of the cement and the specially-shaped processed bone particles of the presently-disclosed subject matter is at least enough to generate the standard chemical reaction for cement setting to occur. When the bone particles are mixed with the cement, the aqueous vehicles temporarily hydrate any exposed collagen in the processed bone particles to allow the bone particle compositions to initially have flow and adherence properties of a standard processed cement. As the water is consumed, the collagen then binds with its surroundings and, at this point, any excess water, or other aqueous vehicle, beyond what is needed for the cement reaction to occur, can be taken up by the porosity of the bone particles or the exposed collagen. In some embodiments, the amount of water absorbed or adsorbed by the particles is about 30 percent to about 50 percent of the weight of the dry bone particles, such that, in certain embodiments, the amount of water or other aqueous vehicle absorbed or adsorbed by the bone particles comprises about 10 percent to about 20 percent of the volume of aqueous vehicle necessary for the setting reaction to occur.

As noted above, a first portion of the bone particles of the presently-disclosed bone particle compositions have a shape that is configured to interconnect with one another when a plurality of those bone particles are included in a bone particle composition of the presently-disclosed subject matter. The terms "interconnect" or "interconnecting" as used herein in reference to the processed bone particles refer to bone particles having shapes that include intersecting surfaces or other structural features that allow the bone particles to interlock and/or more readily interact with one another, as opposed to irregularly-shaped, simple cylindrical, or spherical bone particles that would be unable to interlock with one another or would be less efficient at creating interconnected pathways by virtue of the association of one bone particle with one or more additional, adjacent bone particles.

Figure 1B:
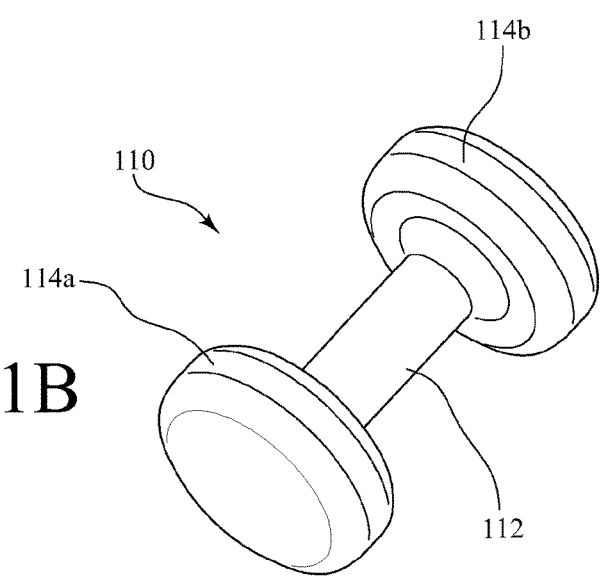
FIG. 1B is a perspective view of another dumbbell-shaped bone particle made in accordance with the presently-disclosed subject matter.
Figure 1C:
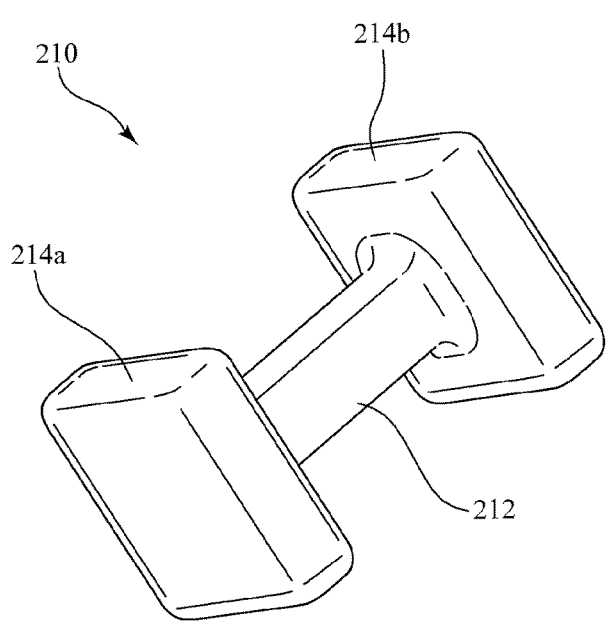
FIG. 1C is a perspective view of a further dumbbell-shaped bone particle made in accordance with the presently-disclosed subject matter.

For example, in some embodiments and as shown in FIGS. 1A-1C and 1E, the bone particles 10, 110, 210, 410 included in the first portion of bone particles are dumbbell-shaped, such that when the dumbbell-shaped bone particles 10, 110, 210, 410 are included in a bone particle composition of the presently-disclosed subject matter, the enlarged ends 14a, 14b, 114a, 114b, 214a, 214b, 414a, 414b of the dumbbell-shaped bone particles 10, 110, 210, 410 overlap and allow contact and engagement of the dumbbell-shaped bone particles along multiple surfaces. In some embodiments of the dumbbell-shaped bone particles, and as also shown in FIGS. 1A-1C and 1E, each bone particle 10, 110, 210, 410 includes two enlarged end portions 14a, 14b, 114a, 114b, 214a, 214b, 414a, 414b that extend laterally away from a longitudinal axis of the center portion 12, 112, 212, 412 of each bone particle. In some embodiments of the dumbbell-shaped bone particles, and as shown in FIG. 1B, a dumbbell-shaped bone particle 110 is provided that includes a center portion 112 with a circular cross-section and two disc-shaped end portions 114a, 114b that extend laterally away from (e.g., are oriented in a direction perpendicular to) the longitudinal axis of the center portion 112. In further embodiments, and as shown in FIG. 1C, a dumbbell-shaped bone particle 210 is provided that includes a center portion 212 with a generally elliptical cross-section and substantially square ends 214a, 214b that extend laterally away from the longitudinal axis of the center portion 212. In yet other embodiments, and as show in FIG. 1E, a dumbbell-shaped bone particle 410 is provided that includes a substantially-flat top surface 418 and a substantially-flat bottom surface 416, and further includes a center portion 412 with a generally square cross-section, and rectangular end portions 414a, 414b that laterally extend away from and are oriented in a direction perpendicular to the longitudinal axis of the center portion 412. Of course, to the extent it may be desired, bone particles of various other interconnecting shapes that would be capable of connecting with one another on multiple surfaces, such as "S-shaped" or "T-shaped" or "C-shaped" bone particles, can also be produced and used in a bone particle composition of the presently-disclosed subject matter without departing from the spirit and scope of the subject matter described herein.

Figure 1D:
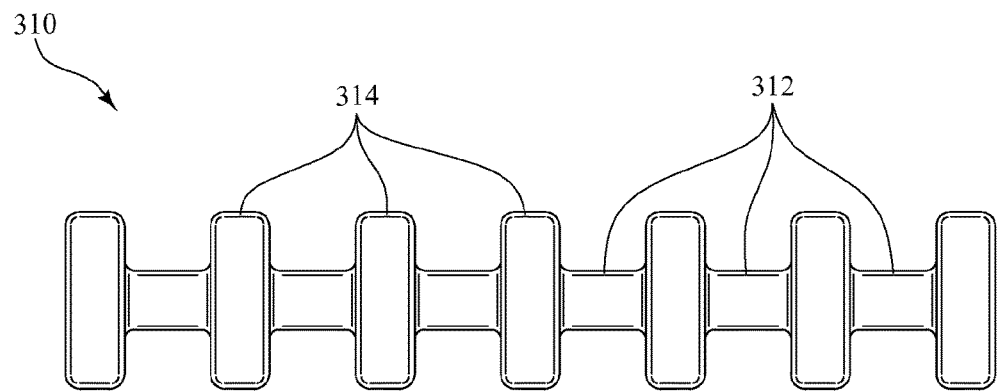
FIG. 1D is a side view of an elongated bone particle made in accordance with the presently-disclosed subject matter.
Figure 1E:
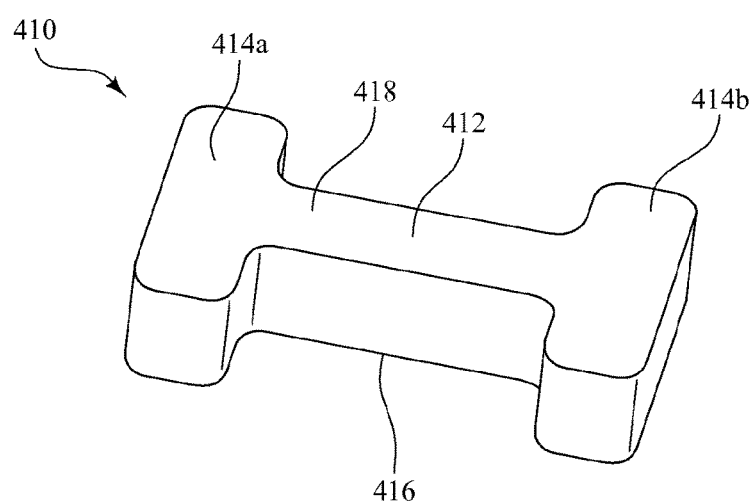
FIG. 1E is a perspective view of yet another dumbbell-shaped bone particle made in accordance with the presently-disclosed subject matter.

Furthermore, in certain embodiments, a number of interconnecting shapes having increased lengths can be provided that are capable of interconnecting with one another on multiple surfaces. For example, and as shown in FIG. 1D, in some embodiments, an elongated bone particle 310 is provided that includes a plurality of rectangular portions 314 and a plurality of center portions 312 aligned along a common longitudinal axis. In the bone particle 310, each of the rectangular portions 314 are oriented in a direction perpendicular to the common longitudinal axis of each center portion 312 and each of the center portions 312 are interposed between the respective rectangular portions 314. As another example of an elongated bone particle made in accordance with the presently-disclosed subject matter, and as shown in FIG. 1F, an elongated bone particle 510 is provided that includes a plurality of enlarged, spherical portions 514 and a plurality of center portions 512 aligned along a common longitudinal axis, where each of the enlarged portions 514 extend laterally away from the common longitudinal axis of each center portion 512, and where each of the center portions 512 are interposed between respective enlarged portions 514.

Figure 1F:
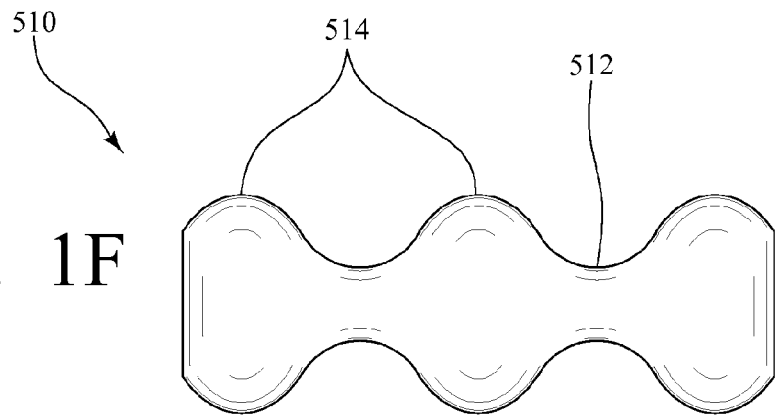
FIG. 1F is a side view of another elongated bone particle made in accordance with the presently-disclosed subject matter.
Figure 1G:
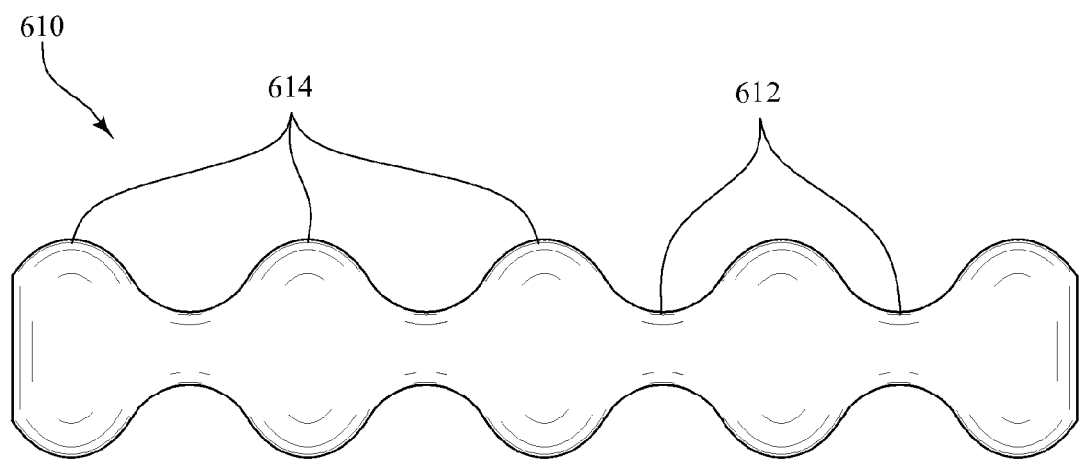
FIG. 1G is a side view of a further elongated bone particle made in accordance with the presently-disclosed subject matter.

In the embodiment shown in FIG. 1F, the bone particle 510 includes three enlarged portions 514. However, it is further contemplated that any number of enlarged portions can be included in a specially-shaped bone particle to produce bone particles of varying lengths without departing from the spirit and scope of the subject matter described herein. For instance, and as shown in FIG. 1G, an elongated bone particle 610 is provided that resembles a number of dumbbell-shaped bone particles placed end-to-end and includes five enlarged, spherical portions 614 and a plurality of center portions 612 aligned along a common longitudinal axis, where each of the enlarged portions 614 also extend laterally away from the common longitudinal axis of each center portion 612, and where each of the center portions 612 are also interposed between respective enlarged portions 614.

In some embodiments of the presently-disclosed subject matter, the interconnectedness of the first portion of the bone particles also increases the compressive, bending, tensile, and shear strength of the bone particle compositions by providing direct loading pathways through contacting other bone particles, which are stronger than the cement matrix. In this regard, in some embodiments, the interconnectedness of the first portion of bone particles is increased by each specially-shaped particle having larger dimensions at its ends compared to its center. For example, the inclusion of bone particles having a dumbbell shape, as described above, or a shape in the form of a capital "I" will have an increased connection to adjacent bone particles when compared to bone particles having a shape in the form of a capital "O," assuming both shapes have similar length and width.

In some embodiments, the interconnecting of the first portion of bone particles allows those particles to increase their resistance to relative elongation displacement, including when they are embedded in a hardened cement. In some embodiments, each bone particle of the first portion of the processed bone particles are further configured to interdigitate with the biologically-resorbable cement such that the strength and mechanical benefits of the presently-disclosed bone particle compositions are further increased. By including interconnecting bone particles in a bone particle composition, the bone particles are able to, in some embodiments, interlock and strengthen the bone particle compositions by the "keystoning" of the cement matrix, a term which is used herein to describe the conversion of tension in the shaped particles to compression in the cement matrix because of the direct interaction between the particle surfaces and the cement contacting surfaces.

Additionally, the interconnecting of the first portion of bone particles also contributes to the enhanced incorporation, remodeling, and resorption of the bone particle compositions when the compositions are placed in a bone defect in vivo by extending three-dimensionally throughout the bone particle composition and bone defect site, and increasing the likelihood that the bone particles communicate not only with one another, but with the fluids and cells outside the cement surface. In other words, by including bone particles having an interconnecting shape in a bone particle composition, portions of the bone particles are capable of extending throughout the composition and into and through the outer surface of the cement structure that is formed when the bone particle composition sets into a solid structure in vivo, which, in turn, allows the composition to be accessible to cells and fluids (e.g., blood supply) from the subject and, ultimately, allows the bone graft composition to be incorporated into a subject.

For a bone particle composition to achieve the objective of becoming completely incorporated into a subject once it is placed in a bone defect, the bone particle composition must generally be rapidly remodeled and replaced with living bone in as short of time as possible, or remodeled such that a new trabecular architecture is restored within the geometry formed by the hardened cement having an interconnected network of included bone graft shapes. As such, it is thought that not only must the bone particle composition be completely incorporated into a host, but the bone particles included in the composition must achieve a "cross-sample bioconnectivity," where the bone particles extend through the composition, once it is placed at the site of a bone defect, and communicate with each other and the outer surface of the bone graft composition to allow access to the grafted region by various cells and fluid from the subject. In this regard, it is also generally thought that as much bone material (i.e., bone particles) should be incorporated into a cement-based bone graft composition as possible and that the bone material should be readily accessible to the cells of a subject and the blood supply of a subject. However, the inclusion of an excessive amount of bone material in a cement-based bone particle composition frequently leads to a bone particle composition that does not exhibit the required mechanical stability and that does not allow the cement to behave like a cement in terms of the handling, flowability, and setting characteristics. Conversely, the inclusion of too little an amount of bone material in a cement-based bone graft composition often leads to a bone graft composition that is not sufficiently incorporated into a subject.

It has now been experimentally observed, however, that the bone particle compositions of the presently-disclosed subject matter, which make use of bone particles having both interconnecting and irregular shapes, are capable maximizing the remodeling capabilities of the composition without also sacrificing the strength and bioconnectivity potential of the compositions. In particular, it has been observed that the composition strength and bioconnectivity can be maintained by including the first portion of bone particles having an interconnected shape, while the remodeling capabilities of the composition can be increased (without decreasing the strength) through the addition of the irregularly-shaped particles. In some embodiments of the presently-disclosed bone particle compositions, the processed bone particles are combined with the biologically-resorbable cement at a concentration of about 1 percent, about 2 percent, about 3 percent, about 4 percent, about 5 percent, about 6 percent, about 7 percent, about 8 percent, about 9 percent, about 10 percent, about 11 percent, about 12 percent, about 13 percent, about 14 percent, about 15 percent, about 20 percent, about 25 percent, about 30 percent, about 35 percent, about 40 percent, about 45 percent, about 50 percent, about 55 percent, or about 60 percent by volume of the bone particle composition.

In some embodiments, the percentage of processed bone particles (particles having both an interconnected shape and an irregular shape) included in an exemplary composition comprises about 5 to about 60 percent by volume of the composition. In some embodiments, the processed bone particles comprise about 5 to about 25 percent by volume of the bone particle composition as such a percentage of processed bone particles has been experimentally observed to be particularly useful for providing a bone particle composition having a desirable combination of strength, bioconnectivity, and remodeling capabilities. In this regard, in some embodiments, the processed bone particles comprise about 18 percent by volume of the bone particle composition. In some embodiments, the first portion of the bone particles (i.e., the particles having an interconnected shape) comprises about 10 percent by volume of the bone particle composition and the second portion of the bone particles (i.e., the irregularly-shaped bone particles) comprises about 8 percent of the bone particle composition. Of course, the amount of bone particles used in an exemplary composition of the presently-disclosed subject matter, including the relative amounts of bone particles having interconnected and irregular shapes, can be selected for a particular application as necessary.

In some embodiments, the infiltration and activity of cells and fluids from the subject depends, at least in part, on the type of bone that is used to fabricate the bone particles of the presently-disclosed subject matter. In some embodiments, the processed bone particles comprise cancellous bone particles that are capable of creating a pathway through the bone particle composition and a bone graft without the need to modify their surface prior to including the cancellous bone particles in the composition. As would be recognized by those skilled in the art, cancellous or spongy bone is comprised of collagenous trabeculae and is typically less dense than cortical bone. As such, when cancellous bone is used to fabricate a processed bone particle, the trabeculae provide tunnel-like spaces in the bone particles that can be used by the cells and fluids of the subject to infiltrate a bone graft in a subject and cause the incorporation and resorption of the bone particle composition.

In other embodiments of the presently-disclosed bone particle compositions, the processed bone particles are comprised of cortical bone. In these embodiments, the outer surface of the cortical bone is typically first demineralized to provide a means to facilitate the movement of cells and fluids to the interior of the bone graft. The term "demineralized" is used herein to refer to the process by which bone mineral or the inorganic portion of the bone is removed to thereby expose the collagen portion of the bone. In this regard, in some embodiments, to prepare a processed bone particle of the presently-disclosed subject matter (e.g., a cortical bone particle), a demineralization process can be used such that the outer surface of the bone is transformed into an exposed collagen layer that is then capable of stimulating and facilitating the infiltration and activity of cells and fluid from the subject into the bone graft. In some embodiments, the processed bone particles are about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, to about 100% demineralized. In some embodiments, by demineralizing the bone particles, the speed with which the bone particle composition is incorporated, remodeled, or resorbed into the subject and replaced by living bone is increased, while the bone particle composition maintains and improves the strength of the subject's bone and the composition itself. In some embodiments, if the processed bone particles are not from an autograft source, the demineralization of the processed bone particles can increase the rate at which the bone particle composition is incorporated into the subject and replaced with living bone from the subject.

As noted above, in some embodiments that make use of bone particles having a demineralized layer, the interconnectedness of the bone particles of the presently-disclosed subject matter further increases the interconnectedness of the osteoinductive demineralized layers covering each particle. In this regard, in certain embodiments, the interconnected network of demineralized bone matrix (DBM) is oriented to resemble a restored trabecular architecture in the incorporating cement material mass, and the specific thickness of the demineralized layer can aid in the osteoconductivity of the end product. In some embodiments, the formation of a demineralized layer, while providing a pathway for the stimulation of activity and the infiltration of cells and fluid into the grafted region, as well as rapid resorption of the bone graft composition, also allows for the addition of an osteoinductive material, an osteogenic material, or both to the surface of the bone particles to thereby further enhance the incorporation of the bone particle composition into the subject and its replacement with living bone from the subject.

The term "osteoinductive material" is used herein to refer to any material that stimulates the migration or differentiation of bone cells to grow and become active at a graft site, while the term "osteogenic material" is used herein to refer to any material that is capable of directly or indirectly contributing to the action of osteoblasts or other cells capable of contributing to new bone growth. In some embodiments, the osteoinductive material that is added to the demineralized bone particles is selected from protein growth factors such as bone morphogenetic proteins (BMPs) and other proteins from the transforming growth factor-beta superfamily. In some embodiments, the osteogenic materials that can be added to the demineralized bone particles include host cells (e.g., osteoblasts, etc.) or stem cells or progenitor cells.

To add an osteoinductive and/or an osteogenic agent to the exposed collagen surface of a demineralized bone particle, the processed bone particles can be soaked in a solution containing the osteoinductive agent, the osteogenic agent, or both, prior to mixing the demineralized bone particles with the biologically-resorbable cement, such that the osteoinductive and/or osteogenic agent simply incorporates into and adheres to the collagen surface. Of course, a number of other methods for linking such an agent to a protein such as collagen are known to those of ordinary skill in the art and can be used without departing from the spirit and scope of the subject matter described herein.

In some embodiments, stem cells can further be added to the bone particles to enhance the incorporation of the bone particle composition into the subject and its replacement with living bone from the subject. As used herein, the term "stem cells" refers broadly to traditional stem cells, progenitor cells, preprogenitor cells, precursor cells, blood cells, platelets, reserve cells, and the like. Exemplary stem cells include, but are not limited to, embryonic stem cells, adult stem cells, pluripotent stem cells, neural stem cells, muscle stem cells, muscle precursor stem cells, endothelial progenitor cells, bone marrow stem cells, chondrogenic stem cells, lymphoid stem cells, mesenchymal stem cells, hematopoietic stem cells, and the like. Descriptions of stem cells, including methods for isolating and culturing them, may be found in, among other places, Embryonic Stem Cells, Methods and Protocols, Turksen, ed., Humana Press, 2002; Weisman et al., Annu Rev. Cell. Dev. Biol. 17:387-403; Pittinger et al., Science, 284:143-47, 1999; Animal Cell Culture, Masters, ed., Oxford University Press, 2000; Jackson et al., PNAS 96(25):14482-86, 1999; Zuk et al., Tissue Engineering, 7:211-228, 2001; Shi, et al., Tissue Engineering Part A, 18(13-14): 1313-21, 2012; and U.S. Pat. Nos. 5,559,022, 5,672,346 and 5,827,735.

In addition to adding various osteoinductive or osteogenic agents, such as stem cells, to the bone particles of the presently-disclosed subject matter, it is further contemplated that a number of additional therapeutic agents can also be added directly to the biologically-resorbable cement prior to mixing it with the processed bone particles. Without wishing to be bound by any particular theory, it is contemplated that the accelerated remodeling and incorporation of the cement due to the presence of the processed bone particles can facilitate a more rapid and more complete release of a therapeutic agent into the subject at the implantation site.

Further therapeutic agents that can be added to the biologically-resorbable cement prior to or after mixing it with the processed bone particles include, but are not limited to: collagen and insoluble collagen derivatives; hydroxyapatite; bisphosphonates and/or other anti-osteoporosis drugs; antiviricides, such as those effective against HIV and hepatitis;

amino acids, peptides, vitamins, and/or co-factors for protein synthesis; hormones; endocrine tissue or tissue fragments; synthesizers; enzymes, such as collagenase, peptidases, oxidases; polymer cell scaffolds with parenchymal cells; angiogenic drugs and polymeric carriers containing such drugs; collagen lattices; biocompatible surface active agents; antigenic agents; cytoskeletal agents; cartilage fragments; living cells, such as chondrocytes, bone marrow cells, mesenchymal stem cells; natural extracts; tissue transplants; bioadhesives; transforming growth factor (TGF-beta); insulin-like growth factor (IGF-1); parathyroid hormone; growth hormones, such as somatotropin; bone digesters; antitumor agents; fibronectin; cellular attractants and attachment agents; immuno-suppressants; and, permeation enhancers, e.g. fatty acid esters such as laureate, myristate and stearate monoesters of polyethylene glycol, enamine derivatives, and alpha-keto aldehydes.

In some embodiments, an antibiotic is added to the biologically-resorbable cement (e.g., the biologically-resorbable cement powder) prior to mixing it with the processed bone particles of the presently-disclosed subject matter. Various antibiotics can be employed in accordance with the presently-disclosed subject matter including, but are not limited to: aminoglycosides, such as amikacin, gentamycin, kanamycin, neomycin, netilmicin, paromomycin, streptomycin, or tobramycin; carbapenems, such as ertapenem, imipenem, meropenem; chloramphenicol; fluoroquinolones, such as ciprofloxacin, gatifloxacin, gemifloxacin, grepafloxacin, levofloxacin, lomefloxacin, moxifloxacin, norfloxacin, ofloxacin, sparfloxacin, or trovafloxacin; glycopeptides, such as vancomycin; lincosamides, such as clindamycin; macrolides/ketolides, such as azithromycin, clarithromycin, dirithromycin, erythromycin, or telithromycin; cephalosporins, such as cefadroxil, cefazolin, cephalexin, cephalothin, cephapirin, cephradine, cefaclor, cefamandole, cefonicid, cefotetan, cefoxitin, cefprozil, cefuroxime, loracarbef, cefdinir, cefditoren, cefixime, cefoperazone, cefotaxime, cefpodoxime, ceftazidime, ceftibuten, ceftizoxime, ceftriaxone, or cefepime; monobactams, such as aztreonam; nitroimidazoles, such as metronidazole; oxazolidinones, such as linezolid; penicillins, such as amoxicillin, amoxicillin/clavulanate, ampicillin, ampicillin/sulbactam, bacampicillin, carbenicillin, cloxacillin, dicloxacillin, methicillin, mezlocillin, nafcillin, oxacillin, penicillin G, penicillin V, piperacillin, piperacillin/tazobactam, ticarcillin, or ticarcillin/clavulanate; streptogramins, such as quinupristin/dalfopristin; sulfonamide/folate antagonists, such as sulfamethoxazole/trimethoprim; tetracyclines, such as demeclocycline, doxycycline, minocycline, or tetracycline; azole antifungals, such as clotrimazole, fluconazole, itraconazole, ketoconazole, miconazole, or voriconazole; polyene antifungals, such as amphotericin B or nystatin; echinocandin antifungals, such as caspofungin or micafungin, or other antifungals, such as ciclopirox, flucytosine, griseofulvin, or terbinafine. In some embodiments, the antibiotic that is included in a bone particle composition of the presently-disclosed subject matter is vancomycin. For further explanation and guidance regarding the use of cements, such as calcium phosphate cements, as drug delivery systems, see, e.g., Verron, et al. Drug Discovery Today. 15(13/14): 547-552 (2010).

Further provided, in some embodiments of the presently-disclosed subject matter, are methods for treating a bone defect. In some embodiments, a method for treating a bone defect is provided that comprises the steps of: providing a bone particle composition of the presently-disclosed subject matter; and administering an effective amount of the bone particle composition to a bone defect site in a subject.

As used herein, the terms "treatment" or "treating" relate to any treatment of a bone defect, including, but not limited to, prophylactic treatment and therapeutic treatment. As such, the terms "treatment" or "treating" include, but are not limited to: preventing a bone defect or the development of a bone defect; inhibiting the progression of a bone defect; arresting or preventing the development of a bone defect; reducing the severity of a bone defect; ameliorating or relieving symptoms associated with a bone defect; and causing a regression of the bone defect or one or more of the symptoms associated with the bone defect.

The term "bone defect" is used herein to refer to any imperfection or discontinuity in the structure of a bone. For example, in some embodiments, the bone defect site is a bone void, or, in other words, an empty space that is typically occupied by bone. As another example, in some embodiments, the bone defect is a bone fracture or a break in the continuity of a bone. As yet another example, in some embodiments, the bone defect site is a site of an intended bone fusion, such as sites where portions of bone are rubbing against one another.

For administration of a bone particle composition disclosed herein, the bone particle compositions are typically administered in an amount sufficient to fill the site of the bone defect, i.e., an "effective amount." Of course, the optimum amount of a bone particle composition used to fill a bone defect will vary depending on the size and/or shape of the particular bone defect being filled. However, determination and adjustment of the amount of a bone particle composition to be used in a particular application, as well as when and how to make such adjustments, can be ascertained using only routine experimentation.

In yet further embodiments of the presently-disclosed subject matter, kits are provided. In some embodiments, a kit is provided that includes a biologically-resorbable cement powder and a plurality of processed bone particles, where the processed bone particles include a first portion having a shape configured to interconnect with adjacent bone particles and a second portion having an irregular shape. In some embodiments of the kits, the biologically-resorbable cement powder and the processed bone particles are packed in separate vessels or are packaged together in a single vessel.

In some embodiments, the bone particles included in the kit are lyophilized or are otherwise dehydrated. In this regard, in some embodiments, the kit further includes an aqueous vehicle for adding to the cement powder, the bone particles, or both the cement powder and bone particles. In some embodiments, the aqueous vehicle can be metered and packaged in a separate vessel such that the vessel includes a precise amount of aqueous vehicle for preparing a bone particle composition having a desired consistency. In other embodiments, the kit further comprises instructions for mixing the cement powder and the bone particles, and then combining that mixture with a prescribed amount of an aqueous vehicle such that a bone particle composition having a desired consistency is produced and can then be administered to a subject.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The presently-disclosed subject matter is further illustrated by the following specific but non-limiting examples.

EXAMPLES

Example 1

Fabrication of Processed Bone Particles Having Interconnecting and Irregular Shapes To fabricate the processed bone particles having both interconnecting and irregular shapes, donor bone tissue was first harvested from a donor via an Organ Procurement Organization (OPO), which coordinates bone donation as donors become available, and was subsequently provided to an American Association of Tissue Banks (AATB)-certified facility, which screened each of the donated bone prior to its use. Specifically, the screening included: obtaining consent from the donor or legal representative of the donor; a review of the donor's medical and social history; a review of the donor's medical records; and a physical assessment of the donated tissue and/or donor. The donated bone tissue was further assessed by: culturing (tissues, environment); serological testing (panel); and quality control release (physical inspection). After the testing, the bone was then processed for delivery via a viral inactivation process (e.g., Allowash®, LifeNet Health Corporation, Virginia Beach, Va.) such as those that make use of a series of chemical rinses and antibiotics.

Figure 3:
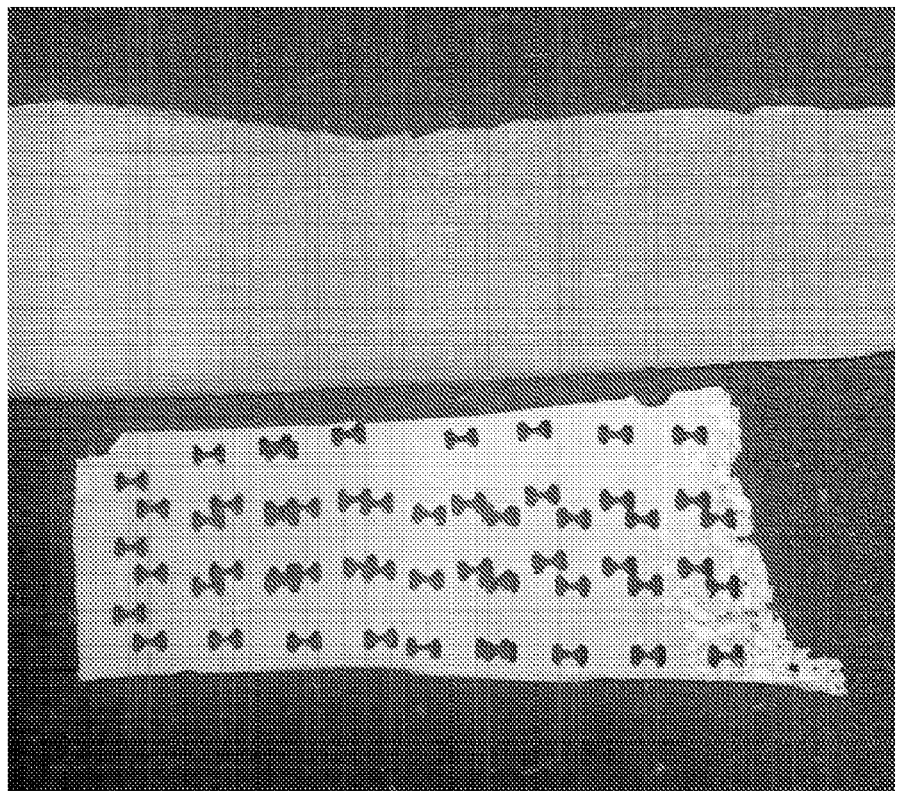
FIG. 3 is an image showing a flat segment of intact bone prior to (top of image) and after (bottom of image) cutting a plurality of the dumbbell-shaped bone particles shown in FIG. 1A from the intact bone.
Figure 4:
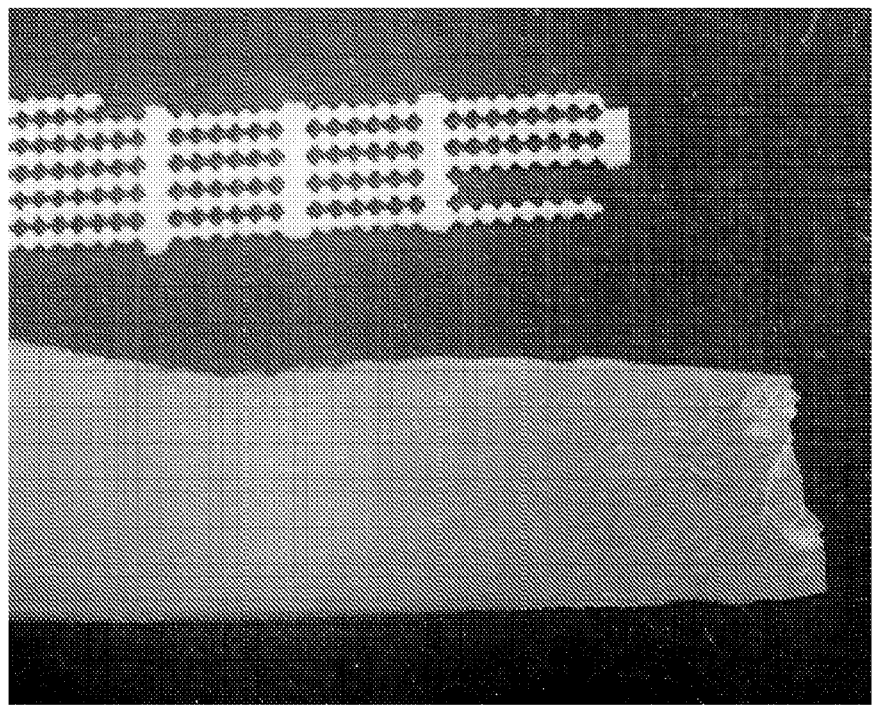
FIG. 4 is an image showing a flat segment of intact bone prior to (bottom of image) and after (top of image) cutting a plurality of the elongated bone particles shown in FIG. 1G from the intact bone.

To shape the donated bone tissue into interconnected and irregular shapes, the cortical shafts of two (2) tibias and two (2) femurs from five (5) donors were utilized. Briefly, the bone was first cut into shorter 2" lengths that could be placed in a custom-made fixture designed to rigidly hold the long axis of the diaphysis parallel to the bench top while having minimum interface with the bone segment so as to not interfere with the cutting blade used to cut the bone. When placed in the fixture, the 2" length was positioned in the fixture with the axis of the bone parallel to the bench top. Making use of such a fixture also allowed the machinery to process as much of the material as possible such that the process not only created less waste, but also did not require the bone segment to be repositioned several times. After securing the bone in the fixture, a computer numerical control (CNC) milling machine with a diamond-sintered cutting disk, a diamond-embedded cutting disk, or a steel fine toothed saw was then used to create elongated flat bone segments (i.e., bone flats) having a thickness ranging from less than 0.5 mm to greater than 1 mm depending on the organic geometry of the bone and the desired application of the processed bone particles (see, e.g., FIGS. 2 and 3). The cutting was performed in a Class 7 cleanroom (or higher standard), and, for most applications, the thickness of the flat segments was 1 mm as the width of the blade used to cut the flat segments resulted in a loss of approximately 0.5 mm of bone material.

In the cutting process, the saw blade rotated on an axis perpendicular to the bench top and to the axis of the bone when using the current fixtures. Typically, a diamond blade was used because it was exceptionally thin and removed only a minimal amount of material when creating the bone flats. In this regard, and without wishing to be bound by any particular theory, it was believed to be possible to reclaim the powdered bone created in this cutting process and utilize the powdered material for other bone tissue products. Additionally, during the cutting process, the disc saw blade and bone tissue were kept cool using a cold air coolant nozzle (i.e., EXAIR®, Exair Corporation, Cincinnati, Ohio; VORTEC®, Illinois Tool Works, Glenview, Ill.) with an inline air regulator assembly to remove moisture from the compressed air source and to filter the air by removing contaminating chemicals or particles.

As the flats were created, the flats were then placed into a dilute alcohol solution (10% ethanol) to reduce contamination from mold, spores, dust, and other particulates. Then, once the CNC machine had cut as many bone flats from the bone segment as possible, without coming in contact with the fixture, the remnant bone segment was removed and a second fixture was used to hold the remnant bone segment for slicing, with the second fixture again being designed to have minimal interface with the bone and allow better access to the bone by the cutting blade. When the CNC cutting process was complete, for each bone segment, the result was a number of bone flats and a small remnant of bone that interfaced with the fixture and could not be cut. Both the flats and the remnant were subsequently placed in separate and labeled containers of dilute ethanol, and were refrigerated until further processing by punching and/or grinding, as described below.

With respect to the punching of the bone particles, a punching process was used to produce bone particles having an interconnected shape. Briefly, the 1 mm flats were removed from the alcohol bath, blotted dry, and are then indexed into a mechanical punch to create bone particles having an interconnected shape that depended on the shape of the particular tool and die utilized for the punching. Generally, the bone flats were indexed by hand to punch new material with each cycle of the punch, and were punched while still somewhat wet to avoid splintering of the bone. The punch was also manually operated in an arbor press, even though it was possible to automate to index material quickly and to punch more material with each cycle.

The punched bone particles resulting from this process thus had interconnected shapes, and were placed in dilute ethanol (10% Ethanol) and refrigerated for short term storage to minimize contamination until further chemical processing. The left over negative space of each bone flat that was not punched was also placed in a separate container of dilute ethanol (10% Ethanol) for storage until it was used in a grinding process.

For the grinding portion of the process, the negative portion of the 1 mm flats and the small remnant of bone left from the CNC cutting process were removed from their respective alcohol baths, blotted dry, and then placed in a grinder. The grinder was then cycled and irregular bone particles were created and sieved to obtain irregularly-shaped particles having a thickness of approximately 1 mm. As part of the sieving process, the smaller material that was outside of the approximately 1 mm specification was removed and recovered for use in other products. Upon sieving, the material in the correct size range was placed in a dilute alcohol bath (10% Ethanol) and the material that was too large was returned to the grinder for further processing. The grinding and sieving process was then repeated until all the material had been processed to either a size range that was within specifications or that was too small for the product, and thus, was retained for use in other products. The material within specification was then again refrigerated in the dilute alcohol solution (10% Ethanol) and refrigerated for short term storage to minimize contamination until chemical processing.

To chemically-process and demineralize the obtained bone particles, a summary of the procedural steps are provided in Table 1 below, where "I.C." or "T" refers to the bone particles having an interconnected shape and where "IRREG" or "P" refers to the bone particles having an irregular shape. All chemical processes were performed in a Class 7 clean room and under a laminar flow hood.

plates were used and were filled with up to 26.316 g of bone tissue, punched particles, or irregularly shaped particles. Each beaker only needed an amount of $H_2O_2$ sufficient to keep the tissue covered while the tissue was agitated by the stir plate (500 ml was the average minimum with the large 4 L beakers, with the maximum being approximately 200 ml per 4.386 g of tissue or 1200 ml of $H_2O_2$ for the full 26.316 g of tissue per beaker). The particles were then left to stir for 30 min, and the $H_2O_2$ was then poured into a waste container.

The processed bone particles were then exposed to a 70% ethanol rinse (operation T30 & P120), where the bone was covered with 70% ethanol (500 ml min. or up to 200 ml per 4.386 g of bone material, 1200 ml max.) and stirred in the ethanol for 14-16 min. The ethanol was then poured into a waste container.

After removing the particles from the ethanol bath, the particles were then subjected to a partial demineralization process using HCl acid (operation T40 & P130). In that

TABLE 1

Chemical Processing and Demineralization Procedure for Bone Particles.

| Demineralization Timing | | | LOW End of Range | | HIGH End of Range | |
|---|---|---|---|---|---|---|
| OPERATIONS | OP. DESCRIPTION | TIME RANGE | I.C. | IRREG | I.C. | IRREG |
| T10 & P100 | Initial Drying & Weight | TIME (hh:mm:ss) (T and P 3:00:00) | 3:00:00 | 3:00:00 | 3:00:00 | 3:00:00 |
| T20 & P110 | H2O2 Rinse and Pour-Off | TIME (hh:mm:ss) (T and P 00:30:00-00:35:00) | 0:30:00 | 0:30:00 | 0:35:00 | 0:35:00 |
| T30 & P120 | 70% Ethanol Rinse (Pre-Demineralization) | TIME (hh:mm:ss) (T and P 00:14:00-00:16:00) | 0:14:00 | 0:14:00 | 0:16:00 | 0:16:00 |
| T40 & P130 | 0.05N HCl Demineralization | TIME (hh:mm:ss) (T 00:48:00-00:52:00, P 00:05:00-00:07:00) | 0:48:00 | 0:05:00 | 0:52:00 | 0:07:00 |
| T50 & P140 | 70% Ethanol Rinse (Post-Demineralization) | TIME (hh:mm:ss) (T and P 00:03:00-00:05:00) | 0:03:00 | 0:03:00 | 0:05:00 | 0:05:00 |
| T10 & P100 REPEATED | Initial Drying & Weight | TIME (hh:mm:ss) (T and P 3:00:00) | 3:00:00 | 3:00:00 | 3:00:00 | 3:00:00 |
| 200, 210, 220, 230, 240 | Weigh out Bone Particles and Fill Lyo Vials | TIME (hh:mm:ss) (T and P ??:??:??) (Two People ~00:02:00?) | 2:00:00 | 2:00:00 | 2:00:00 | 2:00:00 |
| | | TOTAL (Sans LYO) | 9:35:00 | 8:52:00 | 9:48:00 | 9:03:00 |
| 250 | Lyophilization | TIME (hh:mm:ss) (T and P 36:00:00) | 36:00:00 | 36:00:00 | 36:00:00 | 36:00:00 |
| | | TOTAL (Include LYO) | 45:35:00 | 44:52:00 | 45:48:00 | 45:03:00 |

As shown in Table 1 above, in the chemical processing and demineralization portion of the process and for the initial drying and weight measurement of the particles (operation T10 & P100), the processed material was first divided evenly between glass drying plates, with punched and irregularly-shaped particles kept separate from one another. All material was evenly distributed on glass trays to maximize the exposed surface area and speed up the drying process. The glass drying trays, covered in the bone particles, were then inserted into a vacuum oven for drying at 40° C. (±2° C.) to not only reduce drying time, but to keep possible contamination to a minimum as the ovens were not located directly in the laminar flow hood and were only located adjacent to the hood. The vacuum on the oven was cycled between 0 and 28 to 30 in. Hg., with the oven vacuum valve being cycled to reduce the vacuum to 0 in. Hg every 15 min. Additionally, every 30 min, the bone material on the glass dry plates was mixed and evenly re-distributed to expose all sides of the material throughout the drying process. The material was dried for a minimum of 3 hrs.

In the next portion of the chemical processing and demineralization procedures, an $H_2O_2$ rinse and pour off (operation T20 & P110) process was used to further aseptically process the particles. In this regard, 4 L beakers and magnetic stir process, the concentration of HCl, the ratio of liquid to bone, and the time were each experimentally evaluated to yield a demineralization layer with a thickness of approximately 150 microns in the processed bone particles having an interconnected shape. The irregularly-shaped ground bone particles had demineralization layers with varying thicknesses due to the varying size of those particles, with some being completely demineralized. Regardless of the extent of demineralization in the particles, however, and again without wishing to be bound by any particular theory or mechanism, it was believed that the demineralization was important to make the bone particles osteoinductive via the exposing of bone-growth-inducing proteins. The thickness of the demineralization layer was also believed to be important because it allowed cellular ingrowth along the layer, similar to forming a pathway.

Subsequent to the demineralization of the particles, the overall combination of punched and ground particles in the finished product included approximately 24% calcium by dry weight. In this regard, to partially decalcify the particles while still allowing the calcified center portion of the particles to have strength unlike a traditional demineralized bone matrix (DBM) that is completely demineralized (the FDA defines a DBM as one that has less than 8% calcium by dry weight), the particles were covered with 0.05 N HCl (using 600 ml per 4.386 g of bone material), and the punched particles were stirred on a stir plate for 48 to 52 minutes while the ground, irregularly-shaped particles were stirred on a stir plate for 3-5 minutes. The HCl was then poured into a waste container.

After the decalcification process, a 70% ethanol rinse (operation T50 & P140) was then used, where the bone particles were covered with 70% ethanol (500 ml min. or up to 200 ml per 4.386 g of bone material, 1200 ml max.) and stirred for 3 to 5 min. The bone particles were then dried to obtain more accurate mass measurements prior to lyophilization and the basing of the final product on a total mass of bone material and mass ratio between punched particles and ground irregular particles.

More specifically, for the lyophilization process, lyophilization vials were filled with dry punched particles and ground irregular particles at a ratio of 10 parts punched particles to 8 parts ground irregular particles by mass. The vials were then lyophilized over a 36 hour period and subsequently packed in a small cooler and kept on dry ice. While on dry ice, the jars were then exposed to low level gamma radiation to achieve sterilization. The containers of bone were then ready to be combined with a desired amount of a biologically-resorbable cement.

Example 2

Comparison of Bone Particle Compositions

To evaluate an exemplary bone composition of the presently-disclosed subject matter, experiments were undertaken to compare an exemplary bone product formulation of the presently-disclosed subject matter to an available commercial product, namely EQUIVABONE® (Etex Corporation, Cambridge, Mass.), that also includes a bone component. In the EQUIVABONE® product, however, the bone component is fully demineralized allograft bone particles that are not specially shaped, despite being promoted as having positive characteristics associated with cements (hardening, strength, etc.) and as being osteoinductive due to the demineralized bone component.

The composition of the presently-disclosed subject matter that was compared with the EQUIVABONE® product used a calcium phosphate (CaP) cement and was 18% partially demineralized bone by total volume. Of the 18%, 10 parts were particles having an interconnected shape, while the other 8 parts were irregularly-shaped particles. In this regard, and expressed as % total mass, the composition of the presently-disclosed subject matter that was tested was approximately 13% bone.

Compared to the composition of the presently-disclosed subject matter that was tested, the competitive product was approximately 75% fully demineralized bone by volume or about 50% fully demineralized bone by total mass of the composition. The reason for the larger difference (volume vs. mass) was believed to be due to the fact that the bone in the EQUIVABONE® product was fully demineralized, so it had less mass per volume. The cement used in the EQUIVABONE® product was also a CaP cement, but it was a nanocrystalline CaP as compared to the CaP used in the tested composition of the presently-disclosed subject matter that made use of a alpha-tricalcium phosphate powder that, upon mixing with a setting solution, formed precipitated hydroxyapatite.

Figure 5:
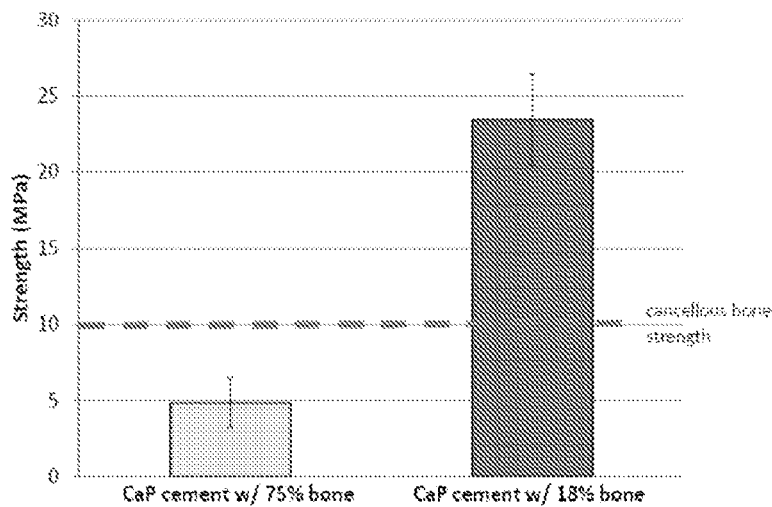
FIG. 5 is a graph showing the results of a 3-point bending test performed to analyze the bending strength of a commercially-available calcium phosphate cement (EQUIVABONE®, Etex Corporation, Cambridge, Mass.) including a bone component (CaP cement w/75% bone by total volume) and a bone particle composition of the presently-disclosed subject matter (CaP cement with 18% bone by total volume)
Figure 6:
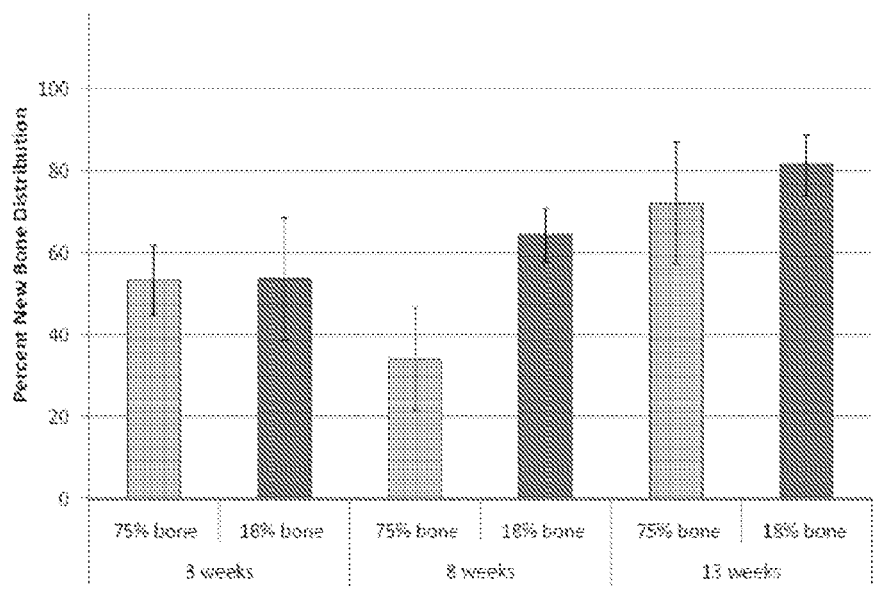
FIG. 6 is a graph showing an analysis of new bone formation tests performed using an in vivo model with New Zealand white rabbits, where a commercially-available calcium phosphate cement (EQUIVABONE®, Etex Corporation, Cambridge, Mass.) including a bone component (75% bone by total volume) and a bone particle composition of the presently-disclosed subject matter (18% bone by total volume) were placed in lateral condyle drill hole defects in the femur of the rabbits and new bone formation was assessed at 3, 8, and 13 weeks.

In these experiments, compression and 3-point bending tests were performed on the hardened cement compositions and new bone formation tests were done using an in vivo model with New Zealand while rabbits, where the cements were placed in lateral condyle drill hole defects in the femur of the rabbits, as described previously and with sample sizes of 10, 10, and 12 at 3, 8, and 13 weeks, respectively. (see, e.g., International Application Publication No. WO 2012/027711, which is incorporated herein by reference in its entirely). As shown in Table 2 below and in FIGS. 5-6, the compositions of the presently-disclosed subject matter containing 18% bone were substantially stronger than the commercially-available product, with the EQUIVABONE® product showing a strength less than cancellous bone in compression tests (FIG. 5) while also showing a remodeling capability (new bone formation; related to osteoinductivity; FIG. 6) comparable to the tested composition of the presently-disclosed subject matter. Upon further analysis of the results, it was thus observed that the combination of interconnected, specially-shaped, partially demineralized bone particles and irregularly-shaped particles enabled less bone to be used in a composition, but yet still allowed sufficient osteoinductivity/remodeling to be achieved. Furthermore, and without wishing to be bound by any particular theory, it was believed that the 10% amount of the shaped particles made it likely that at least two interconnected paths would be present through the cement composition.

TABLE 2

Comparison of Bone Particle Compositions

| Loading Mode | 75% bone by volume; 50% bone by mass | 18% bone by volume; 13% bone by mass |
|---|---|---|
| Compression Ultimate Stress (Mpa), N = 10 | 4.8 (SD = 1.6) | 23.5 (SD = 3.0) |
| 3-Pt Bending Ultimate Stress (Mpa), N = 10 | 3.5 (SD = 1.3) | 4.7 (SD = 2.6) |

Example 3

Evaluation of Strength, Bioconnectivity, and Utilization of Processed Bone Particles To enhance the balance of composition compressive strength, bioconnectivity, and utilization of processed bone particles, additional mechanical testing experiments were performed. In these experiments, the base material was again a commercial-grade calcium phosphate cement, including an alpha-tricalcium phosphate powder that, upon mixing with a setting solution, formed precipitated hydroxyapatite. When this powder mixture was mixed with water in a 2.6:1 powder-to-water ratio by weight, a paste formed that was then capable of setting within fifteen minutes into a solid mass. Bone was processed as described above (see Example 1), yielding specially-shaped particles approximately 2.5 mm in length, 1.5 mm in width at each end, and 1 mm thickness on average with a 0.5 mm wide central portion (see, e.g., FIG. 1A), along with a variety of irregularly-shaped particles. The largest irregularly-shaped particles in the compositions had a maximum dimension of 1.18 mm, and the smallest irregularly-shaped particles had a minimum dimension of 106 µm. Various combinations of amounts (e.g., volume ratios) of each of the processed bone particles were then added to the premixed cement powder, and the compressive strength of the set compositions was tested.

Figure 7:
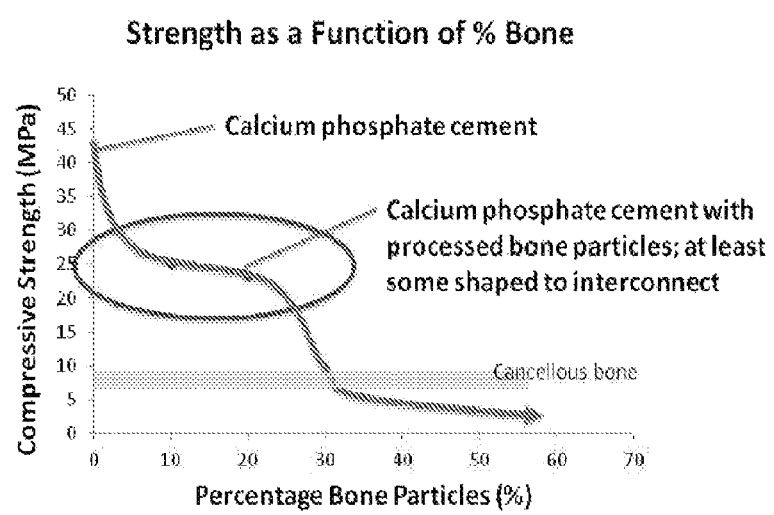
FIG. 7 is a graph showing strength as a function of the percent volume of bone particles included in a composition of the presently-disclosed subject matter.

Upon analysis of the results, and due to the inherent strength of the calcium phosphate cement used, there was an immediate drop in compressive strength once bone particles were added to the composition (FIG. 7). However, the graph generated from the results also showed an unexpected result of a plateau in which the compressive strength of the composition was maintained when the processed bone particle volume fraction was between approximately 5% and 25%. In this regard, it was believed that while the relative decline in compressive strength may vary depending on the cement used, a similar plateau over a bone volume fraction range would be maintained with other biologically-resorbable cements as well. Furthermore, it was also believed that, at the low end of the aforementioned bone volume fraction range (5%), it would be preferable to use only processed bone particles shaped to interconnect as an estimated 5.2% volume fraction of bone particles having an interconnected shape was thought to be required in order to achieve a threshold bioconnectivity in the compositions.

In view of the foregoing tests, it appeared that a cement-based composition of the presently-disclosed subject matter comprised of approximately 18% processed bone particles (10 parts shaped to interconnect, and 8 parts irregularly shaped processed particles) provided a sufficient and desirable composition in terms of strength and bioconnectivity. The 10% of the specially-shaped particles provided both maintenance of composition strength and assurance of bioconnectivity throughout the composition, while the 8% irregularly shaped particles added to the remodeling capabilities of the composition without sacrificing strength. Moreover, the combination of specially- and irregularly-shaped bone particles maximized the use of the bone material, which is of high commercial importance due to the cost of allograft bone. Of course, for applications where strength is less of a concern (i.e., dental, or spinal fusion where rods are providing the structural support) and biological activity/remodeling capability of the cement is the chief concern, a composition comprising 50-60% processed bone particles can be used, and the cement will still set (above 60% bone, not likely to set). Additionally, while a calcium phosphate cement was used in the foregoing example due in part to its strength properties, for other applications, a different (weaker) calcium salt may be preferentially used.

Throughout this document, various references are mentioned. All such references are incorporated herein by reference, including the references set forth in the following list:

REFERENCES

1. International Patent Application Publication No. WO 2012/027711, of VOOR, et al., entitled "Composition and Methods for Treating Bone Defects," filed Aug. 26, 2011.
2. U.S. Pat. No. 8,197,483 to FAULHABER, et al., entitled "Surgical Bone Punch," issued Jun. 12, 2012.
3. U.S. Pat. No. 6,998,135 to SUNWOO, et al., entitled "Demineralized Corticocancellous Bone Sheet," issued Feb. 14, 2006.
4. U.S. Pat. No. 6,962,592 to GATTURNA, et al., entitled "Allograft Implant Cutting Machine," issued Nov. 8, 2005.
5. U.S. Pat. No. 6,776,800 to BOYER, II et al., entitled "Implants Formed With Demineralized Bone," issued Aug. 17, 2004.
6. U.S. Pat. No. 5,899,939 to BOYCE, et al., entitled "Bone-Derived Implant For Load-Supporting Applications," issued May 4, 1999.
7. U.S. Pat. No. 5,464,439 to GENDLER, entitled "Flexible Membranes Produced From Organic Bone Matrix For Skeletal Repair And Reconstruction," issued Nov. 7, 1995.
8. U.S. Pat. No. 5,437,675 to WILSON, entitled "Polygonal Bone Punch," issued Aug. 1, 1995.
9. U.S. Pat. No. 4,008,720 to BRINCKMANN, et al., entitled "Blade With Irrigation Tubes," issued Feb. 22, 1977.
10. International Patent Application Publication No. WO 2013/047936A1 of SONG, et al., entitled "Manufacturing Method For Fibrous Demineralized Bone Matrix," issued Apr. 4, 2013.
11. U.S. Pat. No. 5,176,685 to Rayhack, entitled "Precision Bone Cutting Guide," issued Jan. 5, 1993.
12. U.S. Pat. No. 5,591,170 to SPIEVACK, et al., entitled "Intramedullary Bone Cutting Saw," issued Jan. 7, 1997.
13. U.S. Pat. No. 6,432,436 to GERTZMAN, et al., entitled "Partially Demineralized Cortical Bone Constructs," issued Aug. 13, 2002.
14. U.S. Pat. No. 6,652,592 to GROOMS, et al., entitled "Segmentally Demineralized Bone Implant," issued Nov. 25, 2003.
15. U.S. Pat. No. 7,674,268 to CUCKLER, et al., entitled "Bone Cutting Apparatus," issued Mar. 9, 2010.
16. U.S. Pat. No. 8,202,539 to BEHNAM, et al., entitled "Demineralized Bone Matrix Composition And Methods," issued Jun. 19, 2012.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A bone particle composition, comprising:
   a biologically-resorbable cement; and
   a plurality of processed bone particles, including
      a first portion of processed bone particles having a shape configured to interconnect with one another, each of the bone particles of the first portion being cut from an intact bone or portion thereof, and each of the bone particles of the first portion having greater dimensions at end portions of each of the bone particles relative to one or more center portions of each of the bone particles, and
      a second portion of processed bone particles comprising ground bone particles having an irregular shape.

2. The bone particle composition of claim 1, wherein each bone particle of the first portion of bone particles is further configured to interdigitate with the biologically-resorbable cement.

3. The bone particle composition of claim 1, wherein the biologically-resorbable cement is a calcium-based cement.

4. The bone particle composition of claim 3, wherein the calcium-based cement is a calcium phosphate cement or a calcium sulfate cement.

5. The bone particle composition of claim 1, wherein each bone particle of the first portion of bone particles is dumbbell-shaped, having a center portion and two enlarged end portions.

6. The bone particle composition of claim 5, wherein each bone particle has a length of about 2.5 mm and a thickness of about 1 mm, wherein the width of the center portion is about 0.5 mm, and wherein each of the two enlarged end portions has a width of about 1.5 mm.

7. The bone particle composition of claim 5, wherein each end portion of each bone particle is substantially rectangular and extends laterally away from a longitudinal axis of the center portion of the bone particle.

8. The bone particle composition of claim 1, wherein each bone particle of the first portion of bone particles includes a plurality of enlarged portions and a plurality of center portions aligned along a common longitudinal axis, each of the enlarged portions extending laterally away from a common longitudinal axis of each center portion, and each of the center portions interposed between respective enlarged portions.

9. The bone particle composition of claim 1, wherein a cross-section of each bone particle of the first portion of bone particles is substantially round, elliptical, square, rectangular, or triangular in shape.

10. The bone particle composition of claim 1, wherein each bone particle of the second portion of bone particles has a dimension of about 0.1 mm to about 1.5 mm.

11. The bone particle composition of claim 10, where each bone particle of the second portion of bone particles has a dimension of about 1 mm.

12. The bone particle composition of claim 1, wherein each bone particle of the first portion of bone particles and each bone particle of the second portion of bone particles is about 5% to about 100% demineralized.

13. The bone particle composition of claim 1, wherein the bone particles comprise cortical bone, cancellous bone, or both cortical and cancellous bone.

14. The bone particle composition of claim 1, wherein the bone particles are selected from the group consisting of autograft bone particles, allograft bone particles, xenograft bone particles, and combinations thereof.

15. The bone particle composition of claim 1, wherein the composition further comprises an osteoinductive material, an osteogenic material, or both.

16. The bone particle composition of claim 1, wherein the composition further comprises an antibiotic.

17. The bone particle composition of claim 1, wherein the processed bone particles comprise about 5 percent to about 60 percent by volume of the bone particle composition.

18. The bone particle composition of claim 17, wherein the processed bone particles comprise about 5 percent to about 25 percent by volume of the bone particle composition.

19. The bone particle composition of claim 18, wherein the processed bone particles comprise about 18 percent by volume of the bone particle composition.

20. The bone particle composition of claim 19, wherein the first portion of the bone particles comprises about 10% by volume of the bone particle composition, and wherein the second portion of the bone particles comprises about 8% by volume of the bone particle composition.

21. The bone particle composition of claim 1, wherein the composition further comprises a stem cell.

22. A method for making a bone particle composition, comprising:
providing an intact bone;
cutting the intact bone along a length of the bone to yield a substantially flat segment of the intact bone;
cutting a first portion of bone particles from the substantially flat segment of the intact bone, each of the bone particles having a shape configured to interconnect with one another, and each of the bone particles having greater dimensions at end portions of each of the bone particles relative to one or more center portions of each of the bone particles;
grinding a remainder of the flat segment of bone to yield a second portion of ground bone particles having an irregular shape; and
combining the first portion of bone particles and the second portion of bone particles in a biologically-resorbable cement.

23. The method of claim 22, wherein the intact bone comprises a bone diaphysis.

24. The method of claim 22, further comprising the step of placing the intact bone in a fixture configured to secure the longitudinal axis of the intact bone parallel to the cutting plane.

25. The method of claim 22, wherein cutting the intact bone comprises cutting the intact bone using a saw blade rotating on an axis perpendicular to the longitudinal axis of the intact bone.

26. The method of claim 22, further comprising the step of demineralizing the first portion and the second portion of the bone particles.

27. A method for treating a bone defect, comprising:
providing a bone particle composition according to claim 1; and
administering an effective amount of the bone particle composition to a site of a bone defect in a subject.

28. The method of claim 27, wherein the bone defect is selected from the group consisting of a bone void, a fracture, and a site of an intended bone fusion.

29. The method of claim 27, wherein administering the bone composition to the site of the bone defect comprises filling the bone defect with the bone composition.

30. A kit, comprising:
a biologically-resorbable cement powder; and
a plurality of processed bone particles, including
a first portion of processed bone particles having a shape configured to interconnect with one another, each of the bone particles of the first portion being cut from an intact bone or portion thereof, and each of the bone particles of the first portion having greater dimensions at end portions of each of the bone particles relative to one or more center portions of each of the bone particles, and
a second portion of processed bone particles comprising ground bone particles having an irregular shape.

31. The kit of claim 30, wherein the processed bone particles are lyophilized.

32. The kit of claim 30, further comprising an aqueous vehicle for adding to the biologically-resorbable cement powder, the processed bone particles, or both the biologically-resorbable cement powder and the processed bone particles.

33. The kit of claim 30, further comprising instructions for mixing the processed bone particles and the biologically-resorbable cement powder.

34. The kit of claim 30, wherein the biologically-resorbable cement powder is contained in a first vessel, and wherein the processed bone particles are contained in a second vessel.

35. The kit of claim 30, wherein the biologically-resorbable cement powder and the processed bone particles are packaged together in a single vessel.

* * * * *